United States Patent
Matsuno et al.

[11] Patent Number: 5,916,219
[45] Date of Patent: Jun. 29, 1999

[54] TIBIAL PLATEAU RESECTION GUIDE

[76] Inventors: Shigeo Matsuno, Miyanomori 3.12.5.13, Chuo-ku, Sapporo, Japan, 064; Carlos Esteban Collazo, 32 Bergen Ave., Ridgefield Park, N.J. 07660; Stuart L. Axelson, Jr., 12 Churchill Dr., Succasunna, N.J. 07876; Michael Eric Gertner, 14 Hendrickson Pl., West Long Branch, N.J. 07764

[21] Appl. No.: 08/797,917

[22] Filed: Feb. 10, 1997

[51] Int. Cl.⁶ .................................................. A61B 17/56
[52] U.S. Cl. .............................................................. 606/88
[58] Field of Search .............................. 606/88, 87, 89, 606/86, 96, 102, 80, 79

[56] References Cited

U.S. PATENT DOCUMENTS

| | | |
|---|---|---|
| 4,211,228 | 7/1980 | Cloutier . |
| 4,524,766 | 6/1985 | Petersen . |
| 4,567,885 | 2/1986 | Androphy . |
| 4,574,794 | 3/1986 | Cooke et al. . |
| 4,646,729 | 3/1987 | Kenna et al. . |
| 4,736,737 | 4/1988 | Fargie et al. . |
| 4,759,350 | 7/1988 | Dunn et al. . |
| 4,773,407 | 9/1988 | Petersen . |
| 4,787,383 | 11/1988 | Kenna . |
| 4,841,975 | 6/1989 | Woolson . |
| 4,938,762 | 7/1990 | Wehrli . |
| 4,952,213 | 8/1990 | Bowman et al. . |
| 5,002,547 | 3/1991 | Poggie et al. . |
| 5,342,367 | 8/1994 | Ferrante et al. . |
| 5,342,368 | 8/1994 | Petersen . |
| 5,451,228 | 9/1995 | Johnson et al. ........................ 606/86 |
| 5,578,039 | 11/1996 | Vendrely et al. ..................... 606/88 |
| 5,628,750 | 5/1997 | Whitlock et al. ..................... 606/88 |
| 5,643,272 | 7/1997 | Haines et al. ......................... 606/80 |

OTHER PUBLICATIONS

Publication of DURACON® The Tibial System, Howmedica Inc., Rutherford, NJ, Pfizer Hospital Products Group, ©1993, 1994.

Publication of DURACON® Howmedica Surgical Techniques, entitled Tibial Components Using Monogram™ Total Knee Instruments, by David S. Hungerford, MD and Kenneth A. Krackow, MD.

*Primary Examiner*—Guy V. Tucker
*Attorney, Agent, or Firm*—Pennie & Edmonds LLP

[57] ABSTRACT

An apparatus and method for tibial alignment which allows the independent establishment of two separate geometric planes to be used as a reference for the cutting of the tibial plateau during total knee arthroplasty. Two separate frame assemblies with telescoping rods are attached to the tibia with a fixed relative angle between them, thereby allowing alignment with the mechanical axis of the bone. A cutting block is mounted on one of the assembly frames and is positioned against the tibia. Stabilizing pins are then placed in the cutting block, allowing the proper tibial plateau resection plane to be created.

8 Claims, 3 Drawing Sheets

TIBIAL PLATEAU RESECTION GUIDE

FIELD OF THE INVENTION

The present invention is directed to an apparatus useful as a tibial plateau resection guide and methods for its use in arthroplastic surgery of the knee. More particularly, the invention relates to an apparatus which utilizes adjustable rods in order to fix a bone saw guide to the anterior portion of a patient's proximal tibia.

BACKGROUND OF THE INVENTION

In replacing the knee joint which has been damaged due to disease or trauma, it is important that the damaged bone at the proximal end of the tibia be removed by cutting it at an appropriate varus/valgus angle and at an appropriate flexion/extension angle. In this manner, the bone cut will be in the correct varus/valgus and flexion/extension alignment, and the proximal end of the tibia can then receive an implant or prosthesis to reconstruct a functioning knee joint. Proper fit and function of the implant will depend on the accuracy of the cut.

Many devices for determining the correct angle of the bone cut are known in the art. The known devices typically include a cutting block which guides a saw blade and an anterior telescoping rod or similar device which extends to a position adjacent the approximate center of the anterior face of the patient's ankle or talus to allow the surgeon to duplicate the mechanical axis of the tibia as a reference guide for the proper alignment of the cutting block with the mechanical axis.

Johnson et al., U.S. Pat. No. 5,451,228 (Johnson) discloses a tibial resector guide having an angularly adjustable head controlled by a thumb actuated slide mechanism. The tibial resector guide disclosed by Johnson includes only one telescoping rod to reference the mechanical axis, but no external side rod or similar means to reference the mid-coronal plane.

Ferrante et al., U.S. Pat. No. 5,342,367 (Ferrante) discloses a tibial cutting guide which does not include any means for external referencing, such as extending rods.

Bowman et al., U.S. Pat. No. 4,952,213 (Bowman) discloses using an intramedullary rod connected to a pivot device carrying the bone saw guide. There is no external referencing rod disclosed in Bowman—rather, the reference used is the intramedullary rod inserted deep into the bone canal.

Petersen, U.S. Pat. No. 5,342,368 (Petersen) discloses a proximal tibial resector guide including an intramedullary rod which is attached at its proximal end to a bar provided for the cutting saw guide. There is no external referencing rod disclosed in Peterson—rather, the reference used is the intramedullary rod inserted deep into the bone canal.

Petersen, U.S. Pat. No. 4,524,766 (Petersen) discloses a surgical knee alignment system including a tibial resection saw guide which is mounted on one telescoping external rod used to reference the mechanical axis. There is no external side rod or similar means disclosed to reference the mid-coronal plane.

Wehrli, U.S. Pat. No. 4,938,762 (Wehrli) discloses a reference system for the implantation of condylar total knee prostheses, including a tibial resection saw guide. The Wehrli system utilizes as a main reference point a screw placed in the pelvis, and includes a number of screws placed into the tibia. Telescoping rods attached to the pelvic bone screw and the tibial bone screw are utilized to position the tibial resection saw guide.

One drawback of the use of intramedullary rods as references is that the anatomy of many patients does not permit an intramedullary rod to be fully inserted. Also, the prior art which utilizes only one external referencing rod adjacent the anterior portion of the bone does not provide a direct and reliable means of referencing the mid-coronal plane. The present invention provides external rods for directly and reliably referencing both the mechanical axis and the mid-coronal plane.

Citation or identification of any reference in Section 2 or any section of this application should not be construed as an admission that such reference is available as prior art to the present invention.

SUMMARY OF THE INVENTION

The present invention is directed to an apparatus useful as a tibial plateau resection guide and methods for its use in arthroplastic surgery of the knee. The apparatus has an alignment system that allows for the independent establishment of two separate geometric planes to be used for angular reference in the placement of a cutting guide for use in cutting of the tibial plateau during knee arthroplasty. The axis formed by the intersection of these two planes is intended to duplicate the mechanical axis of the tibia. An angular relationship between the bone and the cutting block is established by fixing a number of adjustable parameters, thereby allowing a surgeon to make a cut in the transverse plane of the tibia at specific, preferred varus/valgus and flexion/extension angles relative to the duplicated mechanical axis.

In one embodiment, the apparatus of the present invention comprises an inverted L-shaped anterior frame assembly placed in the sagittal plane and an inverted L-shaped medial frame assembly placed in the coronal plane. The two frame assemblies are attached to one another, preferably removably attached, such as at the midpoint of the tibial plateau, at a constant angle to one another, such as 90 degrees. The anterior frame assembly, which is placed in the sagittal plane, has a first end and a second end, and has a pivot block, a pivot arm, a support arm, a removably attached cutting block (cutting saw guide) and a telescoping rod which can be extended to the center of the anterior face of the distal end of the tibia, i.e., the center of the talus or ankle. The medial frame assembly placed in the coronal plane has a first end and a second end, and has a top bar and a telescoping rod which can be extended to the center of the subject's malleolus.

The two interlocking frame assemblies are assembled on the tibia, one adjacent the anterior portion of the tibia and one adjacent either the lateral or medial portion of the tibia. It is anticipated that most surgeons will prefer to position the side frame assembly on the medial side rather than the lateral side due to the fact that the patella is usually everted to the lateral side during surgery. For simplicity, the side frame assembly will be referred to herein as the medial frame assembly. Additionally, while the surgeon may attach either the anterior frame assembly or the medial frame assembly first or may attach both frame assemblies to the tibia simultaneously, it is anticipated that most surgeons will attach the anterior frame assembly first, followed by the medial frame assembly. A first anchoring pin is placed through the pivot block into the approximate center of the top of the tibia. The frontal telescoping rod is then extended downward and a rod hinge is rotated in the required direction until the end of the rod is placed directly over the end of the tibia. The rod hinge can then be maintained in a fixed position by turning a thumb screw. The pivot block is fixed in place by means of a secondary pin which anchors it to the tibial plateau and prevents the apparatus from rotating. A cutting block is removably attached, either at a fixed or at an adjustable angle, to a proximal portion of the anterior frame assembly. Adjustments to the angle of each frame assembly and to the height of the cutting block can be made and locked into place.

The two frame assemblies have a fixed angle of 90 degrees between them, thereby providing direct and reliable references to the mid-coronal plane and to the mechanical axis. This facilitates the reconstruction of the tibial mechanical axis.

The present invention also provides for a method of using the tibial resection guide in knee arthroplasty. The method includes attaching a first frame assembly to the tibia and attaching a second frame assembly to the first assembly which interlocks the assemblies at angle of 90 degrees. A frontal telescoping rod which extends downwards from the anterior frame assembly is placed adjacent to the approximate center of the distal end of the tibia or talus. A medial telescoping rod which extends downwards from the medial frame assembly is placed in the approximate center of the malleolus. In order to set the medial telescoping rod in the center of the malleolus, the surgeon may have to adjust the flexion/extension angle of the cutting block and/or rotate the cutting block in the transverse plane around the first anchoring pin. In order to rotate the cutting block, the second anchoring pin must be removed and replaced at a new location. Due to the fixed relationship between the cutting block and medial telescoping rod, varying the flexion/extension angle of the cutting block also varies the flexion/extension angle of the medial telescoping rod by the same amount. A stylus is then used to measure the resection guide height.

DETAILED DESCRIPTION OF THE INVENTION

The present invention is directed to a tibial alignment system that allows the independent establishment of two separate geometric planes to be used for angular reference in the cutting of the tibial plateau during partial or total knee arthroplasty. The reference planes intersect one another at a fixed relative angle. The axis formed by the intersection of these two planes is intended to duplicate the mechanical axis of the tibia, which represents an imaginary line connecting the approximate center of the proximal and distal ends of the bone. A predetermined angular relationship exists between the reconstructed mechanical axis and the surface of the cutting block that determines the attitude of the bone cut.

Figure 1:
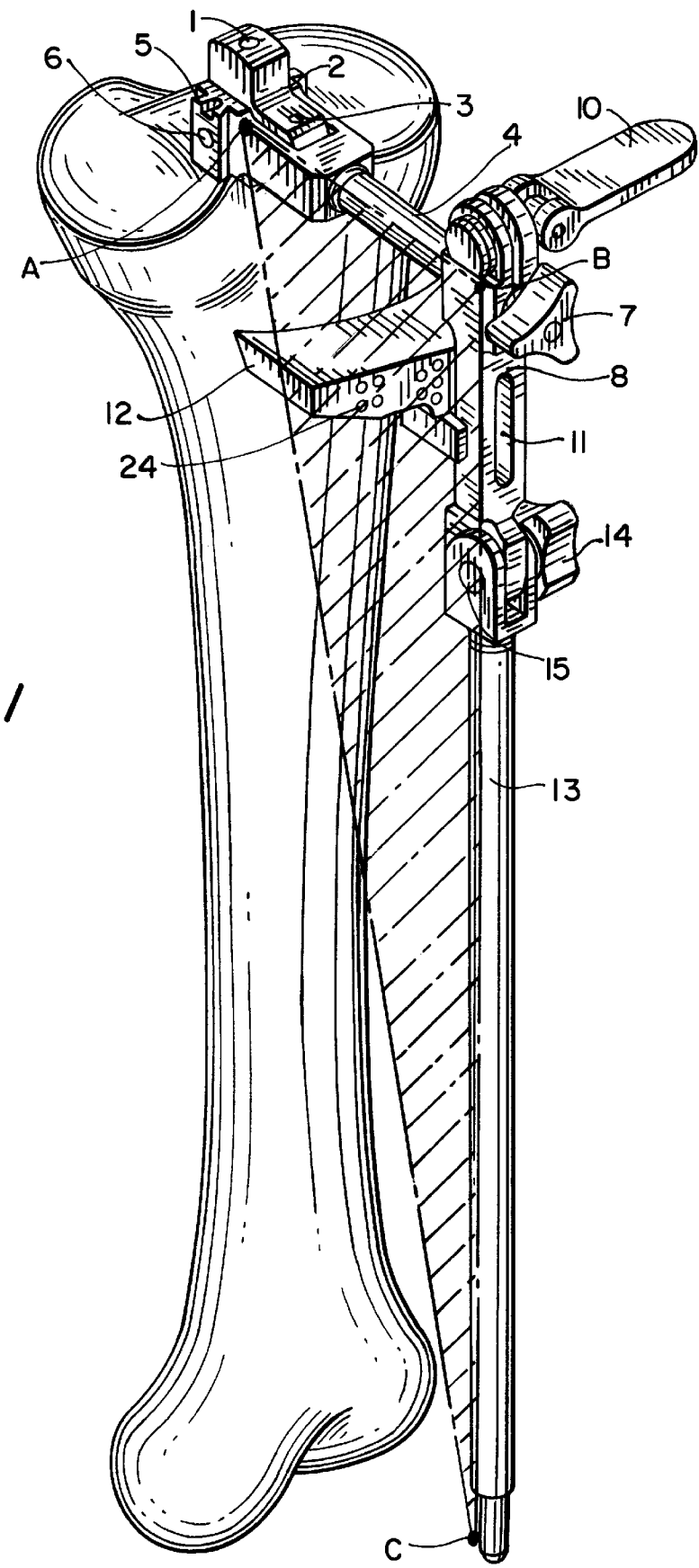
FIG. 1 is a perspective view of the anterior frame assembly, the portion of the tibia it is attached to, and the sagittal reference plane.

FIG. 1 shows the anterior frame assembly and the sagittal plane. A primary anchor pin (not shown) anchors the entire assembly to the approximate center of the top of the tibia. The anterior frame assembly is composed of five main elements: pivot block (2), pivot arm (4), support arm (8), cutting block (12), and frontal telescoping rod (13).

The primary anchor pin runs through the pivot block (2) at a hole or aperture (1). The pivot block (2) itself is pivotally attached to the posterior end of the pivot arm (4) at a hinge point (6) which allows rotation of the pivot arm about the axis in the direction of the sagittal plane. Additionally, the pivot block (2) and attached pivot arm (4) can swivel about the first anchor pin at hole (1). After the surgeon has positioned the cutting block in close proximity to the front of the tibia with the longitudinal axis of the cutting block approximately parallel with hole or aperture (1) at the approximate center of the top of the tibia, a secondary anchor pin (not shown) is placed in secondary hole or aperture (3) to secure the entire anterior frame assembly in place. At the anterior end of the pivot arm (4), a thumbscrew or lever (7) can be turned to tighten the grip of the pivot arm against the pivot block (2). At the posterior end of the pivot arm (4), two grooves (or dovetail) (5) are provided at each side for attachment of the medial frame assembly.

The pivot arm (4) itself fits through an aperture (9) near the proximal end of the support arm (8). The support arm (8) slides back and forth on the pivot arm (4), and can be tightened against the pivot arm by a thumbscrew or lever (10) located adjacent the aperture (9). The support arm (8) itself has an elongated aperture (11) in its center through which a screw (not shown) is inserted to removably attach the cutting block (12) to the support arm (8). The support arm (8) is pivotally attached at its distal end to a frontal telescoping rod (13). The frontal telescoping rod (13) is allowed to swivel back and forth along the sagittal plane and may be locked into a position by tightening a thumb screw (14) at the hinge (15) where the support arm (8) interconnects with the frontal telescoping rod. Frontal telescoping rod (13) can also swivel perpendicularly to the sagittal plane prior to locking thumbscrew or lever (10).

The cutting block (12) is able to move up and down the elongated aperture (11) in the approximate center of the support arm (8). A screw (not shown) fits through the elongated aperture (11) and allows tightening of the cutting block (12) against the support arm (8). This allows the cutting block to be stabilized at an optimal position along the tibia so that the surgeon can cut at the correct tibial plateau. A stylus (not shown) is used to set the depth of the cut at the level desired by the surgeon.

The sagittal reference plane where the anterior frame assembly lies is defined by points A, B, and C, as shown in FIG. 1. Point A lies in the approximate center of the tibial plateau, point B is the intersection of the support arm (8) and pivot arm (4), and point C lies at the distal tip of the frontal telescoping rod (13), which is placed at the approximate center of the anterior face of the distal end of the tibia or ankle.

Figure 2:
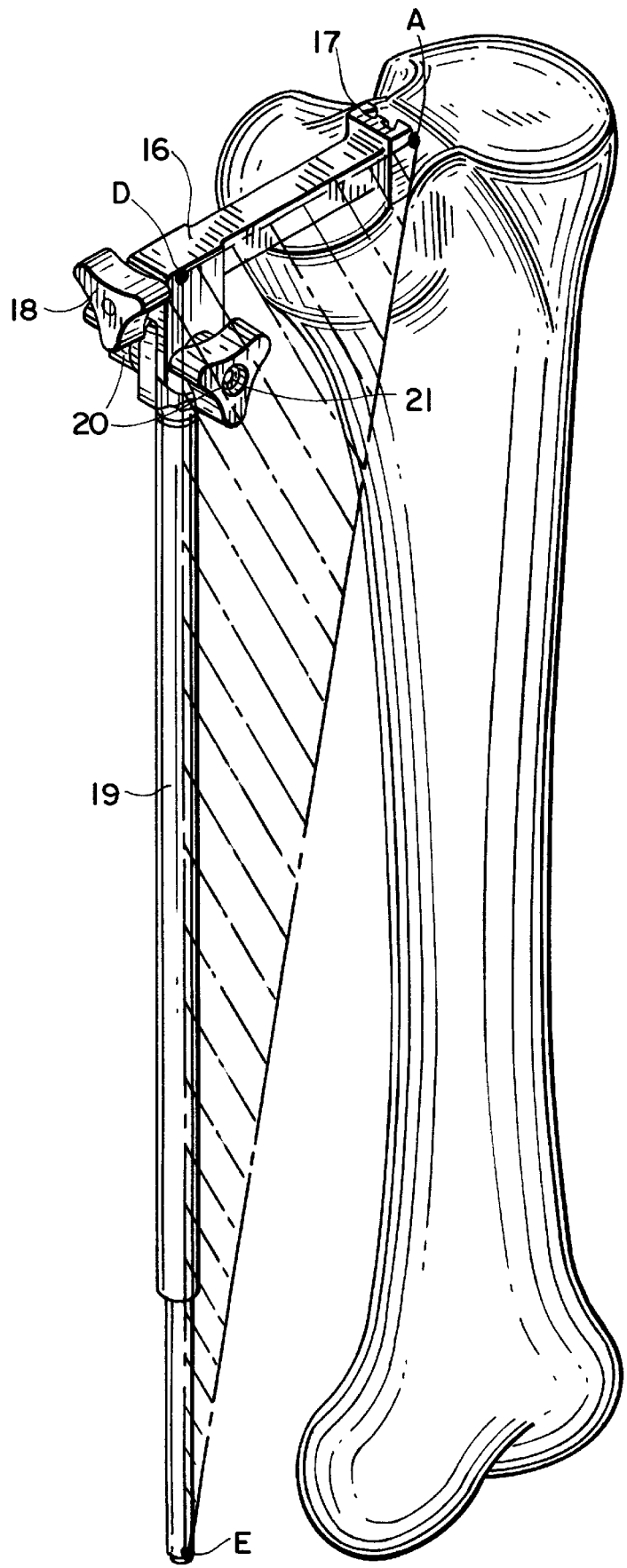
FIG. 2 is a perspective view of the medial frame assembly, the portion of the tibia it is attached to, and the coronal reference plane.

FIG. 2 shows the medial frame assembly and the coronal reference plane. The medial frame assembly is attached, preferably removably attached, to the pivot block (2) of the anterior frame assembly and extends in the coronal plane.

The proximal portion of the medial frame assembly is a top bar (16) which removably attaches at its proximal end to the pivot block (2) of the anterior frame assembly by mating dovetail (17) of the top bar (16) which engages dovetail or grooves (5) of pivot block (2). A thumbscrew (18) is attached to the distal end of the top bar (16), which allows tightening of the medial frame assembly at the proximal end. The top bar (16) is attached at its distal end to the medial telescoping rod (19) which extends downwards perpendicular to the top bar. There are two thumbscrews (20) at the hinge (21) which connects the top bar (16) to the medial telescoping rod (19), and which allow for tightening of the medial frame assembly in its final position during alignment. This hinge (21) enables the medial telescoping rod (19) to swivel along the coronal plane. In use, the distal end of telescoping rod (19) is brought in close proximity to the approximate center of the malleolus on the medial face of the distal end of the tibia, after which thumbscrews (18) and (20) are tightened.

The coronal reference plane is defined by points A, D, and E. Point A lies on the approximate center of the tibial plateau at the very top of the tibia. Point D lies at the intersection of the top bar (16) and the medial telescoping rod (19). Point E lies at distal end of the medial telescoping rod (19), at the approximate center of the malleolus.

Figure 3:
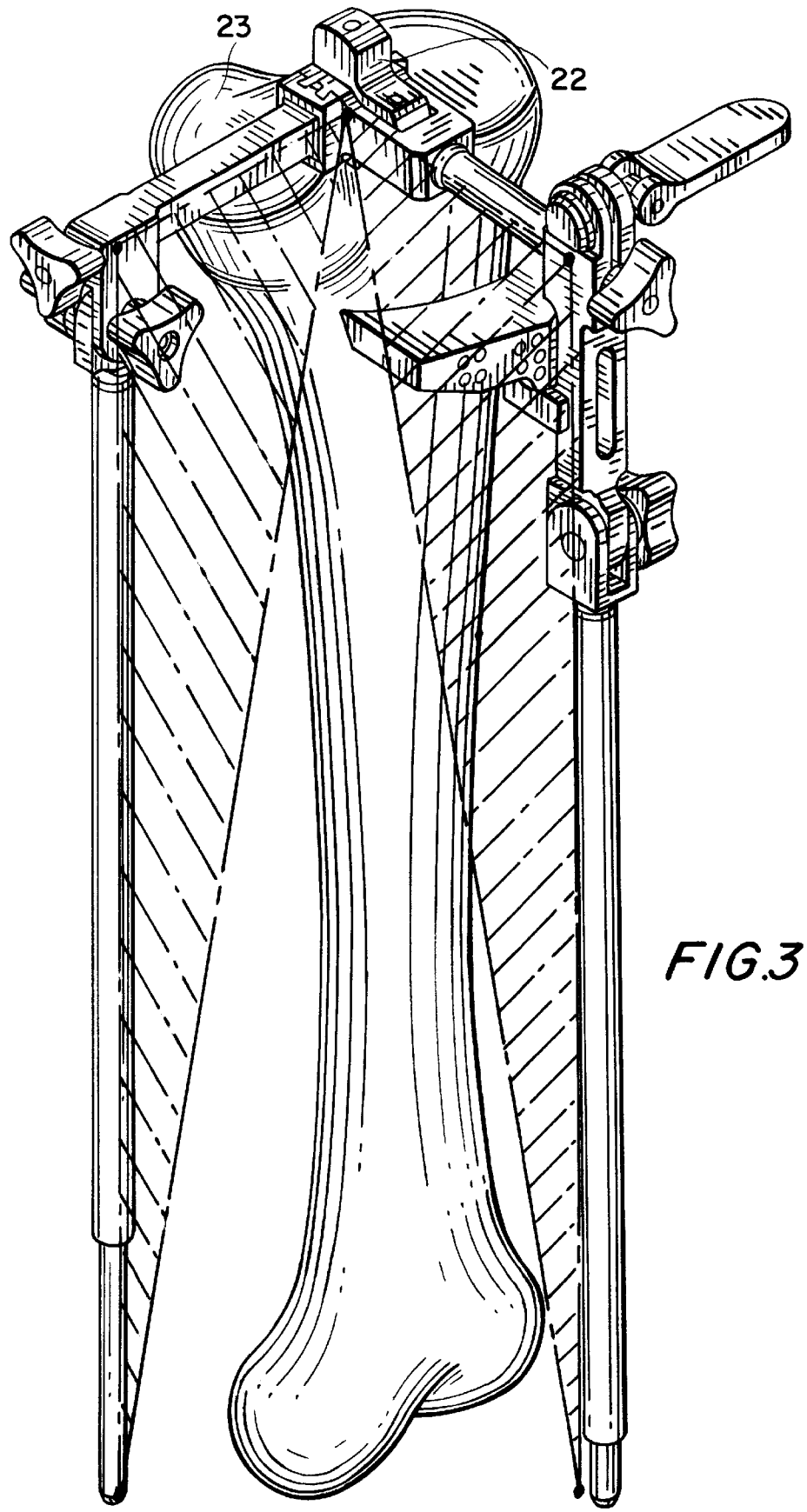
FIG. 3 is a perspective view of the entire apparatus, and the two reference planes and demonstrates the interlocking of the two frame assemblies.

FIG. 3 shows a survey view of the entire apparatus (22) and the manner by which the anterior and medial frame assemblies interlock and fit over the tibia (23). Both the sagittal and coronal reference planes are shown in this view.

The apparatus is assembled and aligned as follows:

The anterior frame assembly is positioned against the tibia in the sagittal plane. With reference to FIG. 1, after placement of the first anchoring pin through hole or aperture (1) at the approximate center of the tibial plateau, the pivot block (2) is placed over this pin and the anterior frame assembly is positioned in close proximity to the anterior face of the tibia with the cutting block (12) touching the patient's leg. Optimal placement of the pin in the sagittal plane can vary due to surgeon preference. The medial side of the knee is preferred since the patella is averted to the lateral side. Once the pivot block (2) is positioned, the secondary anchoring pin is placed into the bone to stabilize and prevent any rotation of the pivot block. In one aspect of the present invention, the support arm (8) is attached to the pivot arm (4) prior to placement of the pivot block (2) into the bone. In another aspect of the invention, the support arm (8) is attached to the pivot arm (4) after placement of the pivot block (2) into the bone.

After the pivot block (2) is secured by a second anchoring pin inserted through aperture (3) in pivot block (2) and the anterior frame assembly is attached, the frontal telescoping rod (13) is extended downward and a rod hinge (15) is rotated in the required direction until the end of the rod is placed directly over the talus. The rod hinge can then be maintained in a fixed position by turning a thumb screw (14). The angle formed between the plane defined by points A, B, C and the cutting block (12) is preferably constant. The cutting block (12) is removably attached to the support arm (8); hence, rotation of one causes equal rotation of the other.

The attachment of the medial frame assembly along the coronal plane proceeds by similar steps. After the medial frame assembly top bar (16) is attached to the anterior frame assembly pivot block (2) by means of the mating dovetails or grooves (17) and (5), the thumbscrew (18) is tightened to secure a tight fit with the pivot block. The medial telescoping rod (19) is then extended downward and rotated in the required direction in the coronal plane to allow the end of this rod to be placed in close proximity to the center of the malleolus. In order to facilitate the placement of the distal end of the medial telescoping rod (19) adjacent the malleolus, the surgeon may rotate the medial telescoping rod (19) about hinge (21) and tighten thumbscrews (20) at the desired position, which merely varies the position of the distal end of the medial telescoping rod (19) and does not affect any other parameter. Due to the fact that the side or medial frame assembly is fixed at a predetermined angle, such as 90°, with respect to the anterior frame assembly, the secondary anchoring pin extending through the pivot block (2) of the anterior frame assembly may have to be removed in order to rotate medial frame assembly top bar (16) to the desired position relative to the mid-coronal plane. In such cases, following the proper placement of medial telescoping rod (19), the secondary anchoring pin is reinserted through pivot block (2) of the anterior frame assembly. Additionally, due to the fixed angular relationship between the medial telescoping rod and the cutting block, varying the flexion/extension angle of the cutting block also varies the flexion/extension angle of the medial telescoping rod by the same amount. Thus, in order to locate the distal end of the medial telescoping rod in close proximity to the malleolus, the surgeon may vary the flexion/extension angle of the cutting block.

After all alignments are made, the surgeon may wish to reassess one or more of the set angles and/or reference points and/or anchoring pin locations, according to personal preference and/or patient anatomy. Then, a plurality of stabilizing pins (not shown) are inserted into the anterior portion of the tibia through selected stabilizing pin apertures (24) in the cutting block (see FIGS. 1 and 3). The cutting block is then detached from the anterior frame assembly and both frame assemblies are removed, leaving behind only the cutting block. A proper tibial plateau resection plane for a saw blade to follow is thereby referenced by the top of the cutting block.

In another embodiment of the invention, the medial frame assembly is configured and dimensioned so as to be attachable to an existing tibial resection guide assembly. The existing tibial resection guide may be any device attachable to the tibia which extends in the sagittal plane and contains a cutting block disposed generally perpendicular to the guide, such as those disclosed in U.S. Pat. No. 5,451,228 or 4,524,766, described above. Such prior art tibial resection guides are generally similar to the structure shown in FIG. 1 of the present application.

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference.

What is claimed is:

1. A tibial resection guide for aligning the tibial plateau with the mechanical axis of the tibia comprising:

(a) an anterior frame assembly which is attachable to the tibia and comprised of a pivot block having a primary hole and a secondary hole adjacent to the primary hole; a pivot arm which is pivotally attached to the pivot block at a hinge which permits the pivot arm to swivel in the sagittal plane; a support arm which extends downward from the pivot arm; a cutting block which is removably attached to the support arm; and a frontal telescoping rod which is attached to the support arm at a hinge which permits the frontal telescoping rod to swivel in the sagittal plane; and (b) a medial frame assembly comprising a top bar and telescoping rod transverse to said top bar, said medial frame assembly configured and dimensioned so as to be attachable to the anterior frame assembly.

2. The apparatus of claim 1 further comprising a primary anchoring pin dimensioned to fit through the primary hole in the pivot block into the tibial plateau.

3. The apparatus of claim 1 further comprising a secondary anchoring pin dimensioned to fit through the secondary hole in the pivot block into the tibial plateau.

4. The apparatus of claim 1 further comprising a hinge disposed at the point where the pivot arm is attached to the support arm; and tightening means operatively associated with the hinge to selectively lock the hinge in a selected position.

5. The apparatus of claim 1 wherein the support arm has an elongated longitudinal aperture therethrough and the cutting block is attached to the support arm by means of a screw which passes through the elongated aperture.

6. The apparatus of claim 1 wherein the cutting block contains one or more holes for insertion of one or more stabilizing pins therethrough for securing the cutting block to the tibia.

7. The apparatus of claim 1 further comprising a hinge disposed at the point where the frontal telescoping rod is attached to the support arm; and tightening means operatively associated with the hinge to lock the hinge in a selected position.

8. A method for positioning a tibial resection cutting block which comprises:

(a) placing a first anchoring pin through an anterior frame assembly and into the approximate center of a tibial plateau, said anterior frame assembly including a removable cutting block having plurality of apertures therethrough;

(b) attaching a medial frame assembly to the anterior frame assembly;

(c) extending a frontal telescoping rod downwardly from the distal end of the anterior frame assembly so that it is positioned adjacent the anterior face of the distal end of the tibia;

(d) extending a medial telescoping rod downwardly from the distal end of the medial frame assembly so that it is positioned adjacent the medial face of the distal end of the tibia;

(e) inserting a plurality of pins through the cutting block apertures to secure the cutting block to the tibia; and (f) removing the anterior frame assembly and the medial frame assembly from the cutting block.

\* \* \* \* \*